(12) United States Patent
Milo

(10) Patent No.: US 8,349,002 B2
(45) Date of Patent: Jan. 8, 2013

(54) ADJUSTABLE ANNULOPLASTY RINGS

(75) Inventor: Simcha Milo, Haifa (IL)

(73) Assignee: QuickRing Medical Technologies, Ltd., Haifa (IL)

( * ) Notice: Subject to any disclaimer, the term of this patent is extended or adjusted under 35 U.S.C. 154(b) by 127 days.

(21) Appl. No.: 12/812,322

(22) PCT Filed: Jan. 16, 2009

(86) PCT No.: PCT/IB2009/005022
§ 371 (c)(1), (2), (4) Date: Jul. 9, 2010

(87) PCT Pub. No.: WO2009/090564
PCT Pub. Date: Jul. 23, 2009

(65) Prior Publication Data
US 2010/0280607 A1 Nov. 4, 2010

Related U.S. Application Data

(60) Provisional application No. 61/021,464, filed on Jan. 16, 2008.

(51) Int. Cl.
*A61F 2/24* (2006.01)
(52) U.S. Cl. .................................................. 623/2.37
(58) Field of Classification Search .................. None
See application file for complete search history.

(56) References Cited

U.S. PATENT DOCUMENTS

| | | | |
|---|---|---|---|
| 4,290,151 A | 9/1981 | Massana | |
| 4,917,698 A | 4/1990 | Carpentier et al. | |
| 5,961,539 A * | 10/1999 | Northrup et al. | 606/232 |
| 6,102,945 A * | 8/2000 | Campbell | 623/2.37 |
| 6,391,054 B2 | 5/2002 | Carpentier et al. | |
| 2001/0021874 A1 | 9/2001 | Carpentier et al. | |
| 2006/0136041 A1* | 6/2006 | Schmid et al. | 623/1.16 |
| 2008/0262609 A1* | 10/2008 | Gross et al. | 623/2.36 |

FOREIGN PATENT DOCUMENTS

| WO | WO03/053289 | 12/2002 |
|---|---|---|
| WO | WO2007/136783 | 5/2007 |

* cited by examiner

*Primary Examiner* — Thomas J Sweet
*Assistant Examiner* — Rebecca Preston
(74) *Attorney, Agent, or Firm* — Fitch, Even, Tabin & Flannery LLP

(57) ABSTRACT

Adjustable annuloplasty rings for repair of a mitral or tricuspid valve which incorporate at least two separate parts that are adjustably interconnectable to create a ring the circumference of which can be changed in dimension. Rings having interconnections at spaced-apart lateral locations, which interconnections allow bidirectional movement to either shorten or lengthen the ring at either such location, afford a surgeon opportunity to make further adjustments to the dimensions of the annuloplasty ring after its initial partial securing to the heart valve tissue and thereby adjust the AP diameter of the valve being repaired. The mating interconnections at two lateral locations on the ring can be constructed so as to allow hinged movement about an axis defined by the interconnections to permit hinged movement between the two separate parts.

10 Claims, 16 Drawing Sheets

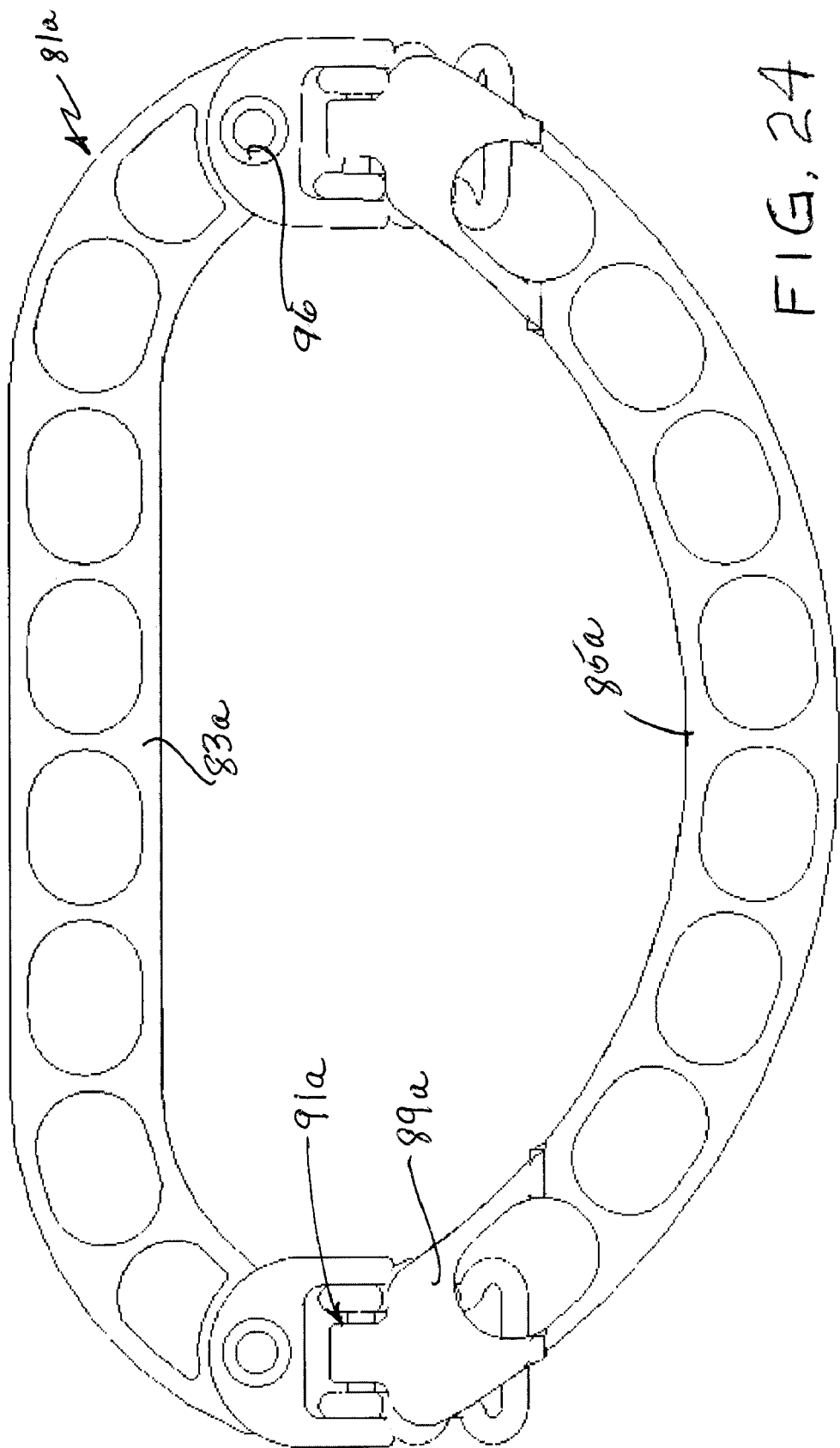

ADJUSTABLE ANNULOPLASTY RINGS

CROSS REFERENCE TO RELATED APPLICATIONS

This application is the U.S. National Stage of International Application Serial No. PCT/IB2009/005022 filed Jan. 16, 2009 which claims priority from U.S. Provisional Application No. 61/021,464, filed Jan. 16, 2008, the disclosures of both of which are incorporated herein by reference.

This application relates to improved annuloplasty rings and more particularly to rings which are adjustable by the surgeon so as to permit a final adjustment to achieve desired leaflet coaptation and valve function.

BACKGROUND OF THE INVENTION

With progress both in understanding of the pathology and pathophysiology of heart valve diseases, and especially of the mitral and tricuspid valves, along with ever-improving surgical skills and technologies, the search for solutions to the disturbing and up to now unsolved problems of treating those valves is steadily increasing. Presently such solutions have involved suturing of a variety of configurations of open and closed rings in association with the valve being repaired. These rings have ranged from very firm shapes to Dacron bands having no stable configuration. Generally, over the past decades, the following two major facts have emerged.

1. Regardless of the ring configuration, its core-materials and/or its pliability, the general technique of using surgical sutures to secure the ring in place, has not changed. The time required to suture a ring in place varies somewhat from surgeon to surgeon but remains more or less the same.

2. A major drawback of the current technique is the inability of the surgeon to make any further change of the ring's configuration once the ring has been sutured to the heart valve tissue. In other words, if the final result in the eyes of the surgeon is less than optimal, he cannot do much to improve the surgical results of his repair once the ring is in place unless he should cut the sutures, and either partially remove the ring or entirely re-implant it.

The implantation system illustrated and described in my published International Patent Application No. WO 03/053289, shows annuloplasty rings and methods for implantation which are designed to allow stapling of a fenestrated ring in place and in this manner reduce the time required for the surgeon to implant an annuloplasty ring while the patient is connected to the heart-lung machine. The disclosure of this application is incorporated herein by reference. However, further improvements that would allow a surgeon to make final, small changes to an annuloplasty ring once it has been secured to the heart valve tissue remain a desire of cardiac surgeons.

SUMMARY OF THE INVENTION

The mitral valve in the interior wall of the human heart has a generally "D" shape. The straight side of the "D" is located at the anterior aspect of the heart, and a great part of the anterior mitral leaflet is attached to this tissue at its base. The semicircular aspect of the mitral valve lies at the posterior side of the heart, and the posterior mitral leaflet is attached at its base to this tissue portion of the wall. The maximal distance between the two leaflets is termed the anterior-posterior (AP) diameter of the valve. Achievement of precision in this AP diameter is one of the most important factors in the repair of a leaking mitral valve because it greatly influences the degree of coaptation of the two leaflets. The desired coaptation at the end of the repair is achieved when the touching free margins of the leaflets in the closed position extend about 8 mm and more.

It has been found that a most significant maneuver on the part of a surgeon will be to be able to optimize the coaptation when an annuloplasty ring is being implanted and that such can be best achieved when the surgeon has the ability to make minor adjustments to, i.e. fine-tune, the AP diameter of the mitral valve. The present invention enables such fine-tuning to take place after initially securing the annuloplasty ring to the heart valve tissue; this allows the surgeon to observe the degree of coaptation that has been initially achieved and assess whether and what adjustments may still be needed.

More specifically, the present invention enables a surgeon to implant a fenestrated or perforated ring by stapling or suturing it to the heart valve tissue and then observe the degree of coaptation achieved by the ring. If such is not considered optimal, the AP diameter may be fine-tuned by making minor adjustments at two different locations where ends of the two generally lineal pieces that comprise the annuloplasty ring are interconnected.

In one particular aspect, the invention comprises an annuloplasty ring which comprises at least two separate parts which are interconnectable to form a complete ring that will encircle a valve to be repaired and which can be adjusted at least two spaced apart locations to change the circumference of the ring.

In another particular aspect, the invention comprises a method of repairing a mitral or tricuspid valve using a two-part interconnectable ring wherein each of the two ring parts is initially partially secured to the heart valve tissue and following adjustment of at least one of said interconnections, final securing of the two ring parts in a final adjusted position is done by additional stapling to the heart tissue or with additional surgical sutures.

In yet another particular aspect, the invention provides an adjustable annuloplasty ring which comprises first and second generally linear interconnectable parts made of generally flat, perforated, biocompatible bar stock material, each said part having a series of apertures spaced along the length thereof and having end portions comprising mating interconnection means, and said interconnection means at the ends of said first part being designed to adjustably connect with said mating interconnection means at the ends of said second part and form a complete ring which is shaped and proportioned to surround a human mitral or tricuspid valve and the circumference of which is changed by adjustment at said mating interconnection means.

In a further more particular aspect, the invention provides an annuloplasty ring which comprises at least two separate parts which are interconnectable to form a complete ring that will encircle a valve to be repaired, having at least 2 pairs of mating interconnections which are constructed to permit both adjustments to the circumference of the ring and hinged movement between said two separate parts, and more particularly hinged movement about multiple axes at each of two lateral locations.

BRIEF DESCRIPTION OF THE DRAWINGS

FIG. 24 is a plan view of another alternative embodiment of a ring shown similar to FIG. 18.

DETAILED DESCRIPTION OF THE PREFERRED EMBODIMENTS

As indicated above, the present invention enables a surgeon, following initially securing a perforated or fenestrated ring to heart valve tissue in association with a mitral or tricuspid valve, to still be able to fine-tune the AP diameter of the valve by making minor changes to the ring itself in order to see if such a change would indeed contribute to the overall quality of the repair by optimizing the coaptation of the leaflets. Such fine-tuning of the implanted ring can be effected either symmetrically or asymmetrically by adjusting one or both of the points of interconnection between two separate generally lineal pieces which make up the ring. In a mitral valve annuloplasty ring, the locations of interconnection will generally correspond to regions located at about the commissures of the valve; however, additional such interconnections (between more than two parts) or interconnections in other sections of ring other than depicted herein might alternatively be used. The adjustment illustrated and described hereinafter is such that the distance between the corresponding trigons is not changed; it is the distance between a generally straight section of the ring and a generally semicircular section of the ring that is changed, as a result of which the AP diameter is accordingly increased or decreased as desired. Even though some inherent, spontaneous, fine-tuning of the heart valve can occur as a result of the freedom of movement that is permitted between such a perforated ring which is secured to the heart tissue by staples seated in enlarged openings or windows in such a ring, this amount may not be as much as desired. Moreover, final stabilization may not be achieved until new scar tissue forms inside the native ring and in-between the staples, and tissue overgrowth occurs, such usually takes place within six months following the implantation of the ring in the valve being repaired. Using the illustrated adjustable annuloplasty rings, significant fine-tuning to achieve optimal coaptation of the leaflets is instantly achieved.

Figure 1:
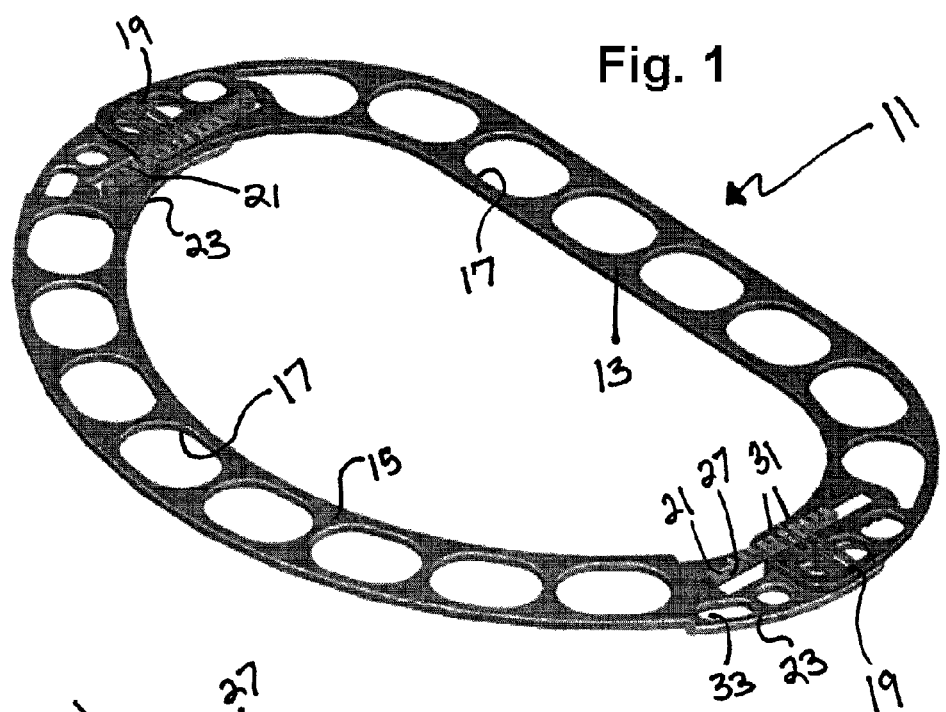
FIG. 1 is a front perspective view of an adjustable two-piece annuloplasty ring designed for repair of a mitral valve which embodies various features of the present invention.
Figure 2:
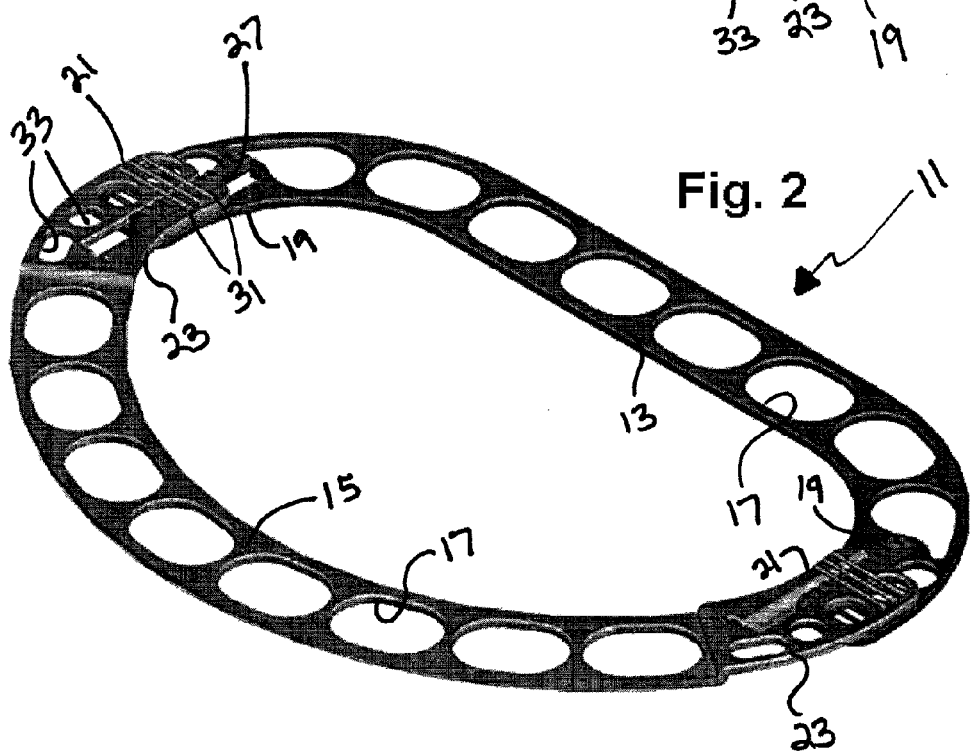
FIG. 2 is a perspective view of the ring of FIG. 1 taken from the opposite or rear side.
Figure 3:
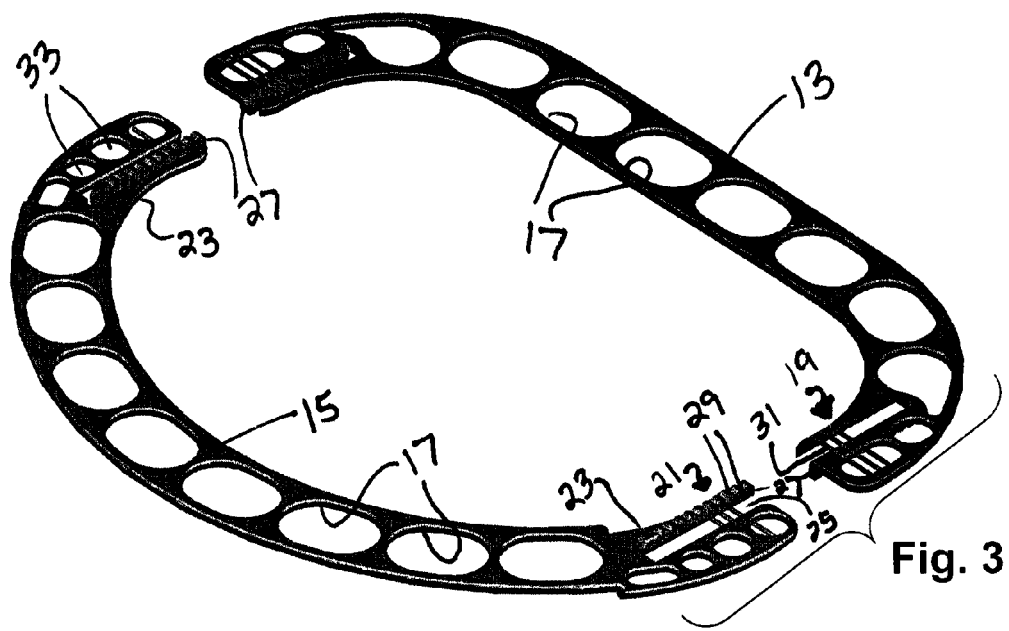
FIG. 3 is an exploded perspective view of the ring of FIG. 1 with the straight and semicircular pieces shown aligned with each other prior to joinder.

Illustrated in FIGS. 1 and 2 is a first embodiment of an adjustable annuloplasty ring 11 designed for repair of a human mitral valve which is formed of two separable lineal pieces or parts. As best seen in the exploded perspective of FIG. 3, the ring 11 comprises a generally straight piece 13 and a generally semicircular piece 15. Although referred to throughout as a straight piece and a semicircular piece for convenience, it should be understood that the straight piece has short bent ends where interconnecting parts are formed and the semicircular piece more resembles a section of an oval. Both the pieces 13 and 15 are linear with a series of elongated apertures or windows 17 formed along the respective lengths thereof to provide a series of spaced-apart openings through which the legs of staples or appropriate suturing can be disposed to secure the ring 11 to the tissue of the heart valve being repaired. The ring parts are asymmetrically shaped and anatomically correspond respectively to the bases of the anterior and the posterior mitral valve leaflets in the areas between the antero-lateral and postero-medial commissures.

The two pieces 13 and 15 are formed with mating interconnecting parts 19 and 21 at their respective ends which allow them to be interconnected to form a complete ring that will encircle a valve to be repaired and in this embodiment provide a generally planar composite structure. The interconnecting parts 19 and 21 are designed to permit the ring to undergo bidirectional movement, i.e. the AP diameter can be either lengthened or shortened by appropriate change at each location of such interconnection. In this embodiment, the interconnecting parts 19 and 21 overlap and are generally similar as each lineal end is formed with slots and contiguous toothed bars; such are formed in a pair of arms which forms the opposite bent ends of the main straight body of the piece 13.

Figure 4:
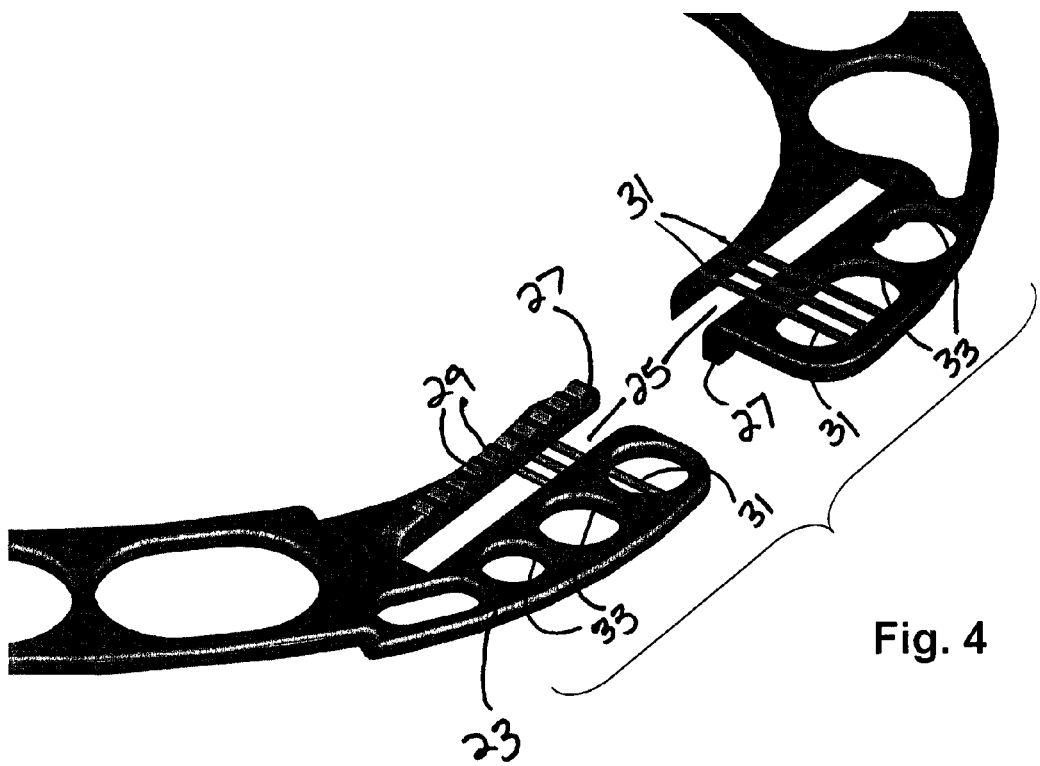
FIG. 4 is a fragmentary view, enlarged in size, of a portion of FIG. 3.

The two pieces 13 and 15 are formed from generally flat bar stock of suitable biocompatible material that will retain its three-dimensional form once it has been shaped. Any suitable biocompatible metal, polymeric or composite material can be used, as well known in this art of prostheses for implantation in the human body. An example of one suitable material would be a biocompatible titanium alloy bar or sheet stock from which the pieces 13 and 15 could be readily formed by laser cutting and/or mechanical punching and shaping. In order to preferably retain the main body portions of two pieces which make up the adjustable ring 11 in the same plane, the end sections of one or both of the pieces are offset or stepped slightly for a distance equal to about the thickness of the bar stock to effect a juxtaposed relationship of the respective ends while the main bodies lie in a single plane. In this embodiment, as best seen in FIG. 4, the end sections 23 of the semicircular piece 15 are stepped rearward so that, in the interconnection, the ends of the straight piece 13 are generally slidably received atop the front surface of the stepped down end sections 23 of the semicircular piece 15.

As mentioned, each of the end sections has a generally similar set of mating interconnecting parts, namely, an open ended slot 25, a contiguous straight bar section 27, which is formed with a plurality of teeth or detents 29, and a plurality of flexible rods or retainers 31 which are spaced apart distances corresponding to the valleys between adjacent teeth so as to provide a bidirectional ratchet-type arrangement that permits incremental adjustment in each of the two lateral locations on the adjustable ring where the respective ends of the two pieces are interconnected. As best seen perhaps from FIGS. 3 and 4, when the respective ends of the pieces 13 and 15 are slidingly mated with each other, the respective bars 27 will be slidingly received in the open ended slots 25. Three thin rods 31 are fixed to the front surface of the straight piece 13, and three are affixed to the rear surface of the semicircular piece 15, in a manner so that they will deflect and allow the passage of the toothed bar 27 therepast. Accordingly, it can be seen that the toothed bars 27 and the spring-like rods 31 provide a bidirectional ratchet-type mechanism which permits the sliding interconnection of the respective ends of the two pieces 13 and 15 to be easily adjusted as a part of the surgeon's implantation of the annuloplasty ring. The elongated windows 17 provide openings through which one leg of a surgical staple can be disposed, or through which suturing can be effected. Such staples may be implanted so as to straddle the outer peripheral edge of the adjustable annuloplasty ring 11 or with the two legs in adjacent windows as desired. A series of smaller openings 33 are located in the mating end sections of the two pieces. The terms front surface and rear surface are used mainly for clarity of description. Because the interconnecting parts 19 and 21 are essentially the same, the ring 11 can be used with either surface in contact with the heart valve tissue.

In a typical installation proceeding, the surgeon will measure the valve to be repaired and then select a ring of appropriate size and adjust the selected ring 11 to the precise size that he believes will have the desired AP diameter dimension. The surgeon will then initially implant the ring by stapling or suturing it to the heart valve tissue, operating through selected windows 17 at sufficient locations so as to effectively reshape the valve as desired. The advantage of the adjustable ring 11 is that, following such initial implantation, the surgeon can observe the degree of coaptation of the leaflets achieved with the ring. Should the degree of coaptation not be optimal, he can change the length of the ring at either lateral location, or at both locations, as for example by engaging the edges of openings 33 in the respective pieces and squeezing the pieces together at one lateral location to cause the teeth 29 to ratchet past the respective rods 31 and shorten the length of that lateral portion of the ring effecting thus the valve's AP diameter. Because the ring 11 is initially attached to the heart valve tissue only by staples or suturing passing through the elongated windows 17, there will be latitude for the ring 11 to shift slightly with regard to the heart valve tissue when such shortening or lengthening at one or both of the lateral locations takes place without creating undesired stretching force on the heart valve tissue at the locations of such stapling and/or suturing. Once optimal coaptation of the leaflets has been achieved, the surgeon completes the implantation by adding additional staples or sutures to secure the ring 11 in its optimal operative position. As part of the final securing, one or more staples or sutures can be placed through the smaller openings 33, including a pair of aligned openings in the juxtaposed end sections of the respective pieces.

Although only two pieces 13, 15 are shown, which have interconnections at two lateral locations for a mitral valve repair, it should be understood that the adjustable annuloplasty ring could be made with three or more pieces having additional interconnections therebetween; such would allow some further adjustment of the respective lengths of other sections of the ring. For example, in a mitral valve repair annuloplasty ring, the segment corresponding to the posterior mitral leaflet base could have such an adjustable interconnection that would, following initial securing of the ring to the valve tissue, allow a change in length that would alter the long axis diameter of the ring. An additional interconnection between two mating sections of the semicircular piece could also be incorporated if desired. Although generally the mating pieces will be made of similar bar stock materials, they could be made of different materials, and the interconnections at different locations on the ring could comprise different structures if desired. Although materials are used which will return to their desired three-dimensional shape, the pieces could be made of materials having stiffness so that they are essentially rigid; however, pieces having various and/or different flexibilities may be used.

In the foregoing description, it was indicated that the adjustable ring would be introduced as an assembly of the two interconnected pieces; although such method is likely, it is not a requirement. For example, if the ring were designed for implantation in a minimally invasive procedure, it might be preferable to introduce each of the pieces separately, assembling them in situ about the valve being repaired by initially attaching one of them first. Moreover, in such a situation, the pieces might be introduced while temporarily attached to a respective holder, which might facilitate the maneuvering of that section of the ring, or the entire ring, particularly in a minimally invasive implantation procedure. Furthermore, if the parts of the ring or the entire ring were to be introduced through a tubular catheter in a minimally invasive procedure, they might be suitably crimped so as to facilitate passing though such a conduit and designed to return to their desired operative shape once freed from the outlet end of such delivery tube. In such an instance, the pieces might be made from a biocompatible shape-memory material such as Nitinol or other such alloy or material. Robotic mechanisms for installing implants of this type in minimally invasive procedures have been developed and are continually being improved. Accordingly, such could be used along with remote-control stapling devices which are known in this art. As mentioned, suitable holders or interfaces temporarily attached to the pieces might be used to facilitate such remote implantation of each of the pieces of such an adjustable annuloplasty ring.

Figure 5:
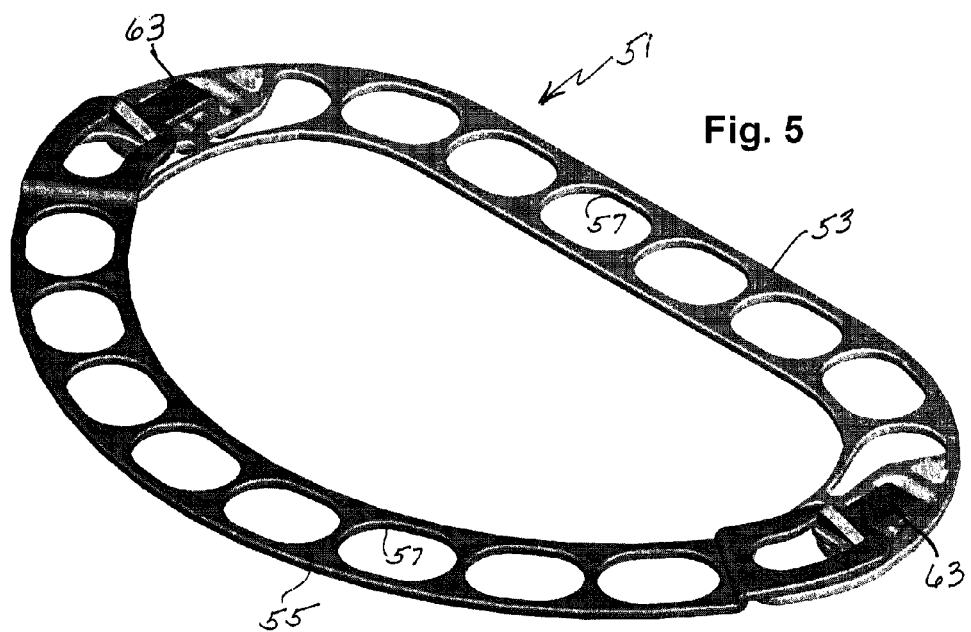
FIG. 5 is a perspective front view of an alternative adjustable two-piece annuloplasty ring embodying various features of the present invention with the two pieces shown interconnected in symmetrical orientation.
Figure 6:
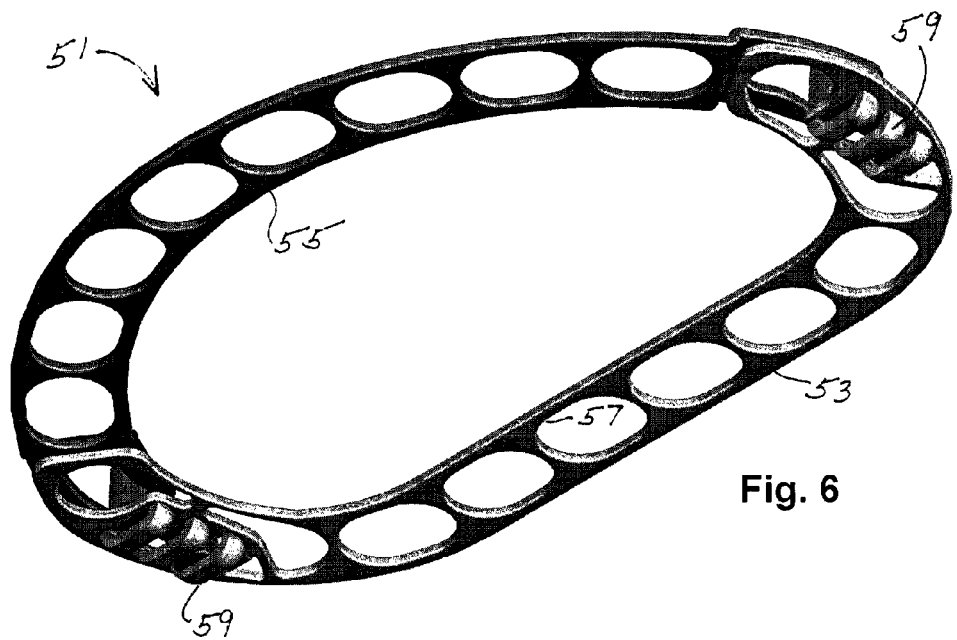
FIG. 6 is a perspective view of the ring of FIG. 5 taken from the opposite or rear side.

Illustrated in FIGS. 5 and 6 is an alternative embodiment of an adjustable annuloplasty ring 51 embodying various features of the invention, which is also designed for repair of a mitral valve. The ring 51 is formed from two pieces or parts: a straight piece 53 having a pair of short, generally parallel arms at its ends, and a semicircular piece 55; both pieces are of a generally linear form, having a plurality of elongated windows or apertures 57 spaced along their lengths. The respective end sections of the pieces 53 and 55 overlap and are formed with mating interconnecting parts 59 and 61 that allow the interconnection of the two pieces into an adjustable complete annuloplasty ring. The interconnecting parts at these two lateral locations of interconnection permit adjustment of the respective length of that lateral section of the ring to one of three different lengths. Again, one or both of the ends of the pieces 53, 55 is stepped up or down so as to provide a composite ring 51 where the main bodies of the two pieces that form the ring lie in the same plane. In the illustrated embodiment, the semicircular piece 55 has its end section 62 stepped upward, i.e. toward the front surface, a distance equal to the thickness of the piece 53 so that the rear surface of the ring (which will lie in contact with the heart valve tissue) is essentially planar. The two pieces 53 and 55 are shown separately viewed from their front surfaces in FIGS. 7 and 8. FIG. 8 illustrates the stepped up end section 62 of the semicircular piece 55, the rear surface of which section will lie in juxtaposition with the front surface of one respective end of an arm of the straight section piece 53.

Figure 7:
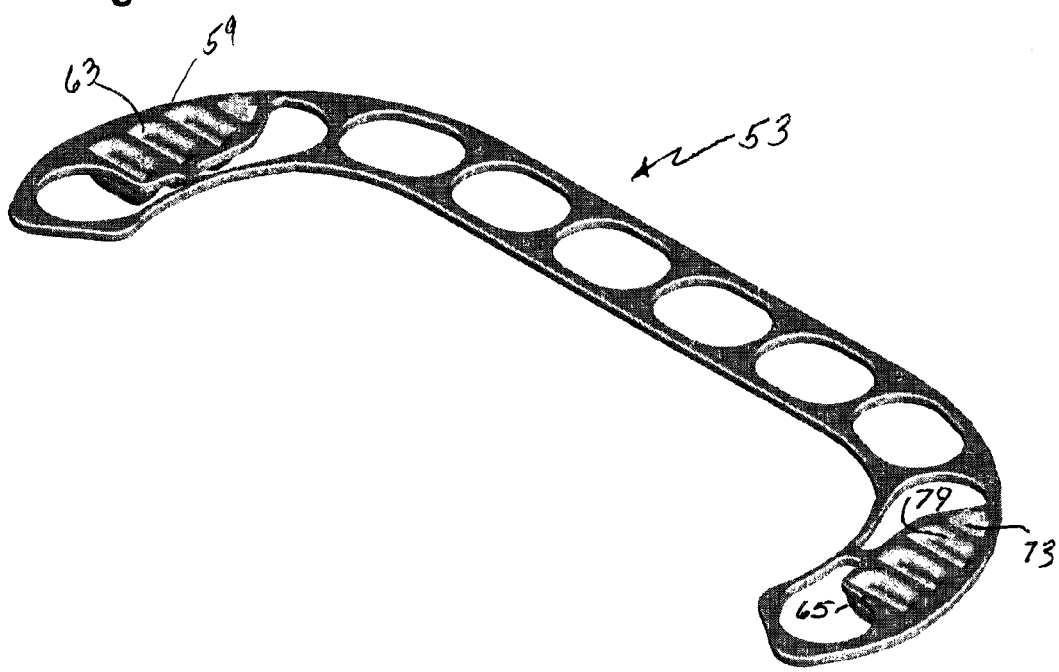
FIG. 7 is a perspective view of the straight piece of the ring of FIG. 5 taken from the front side.
Figure 8:
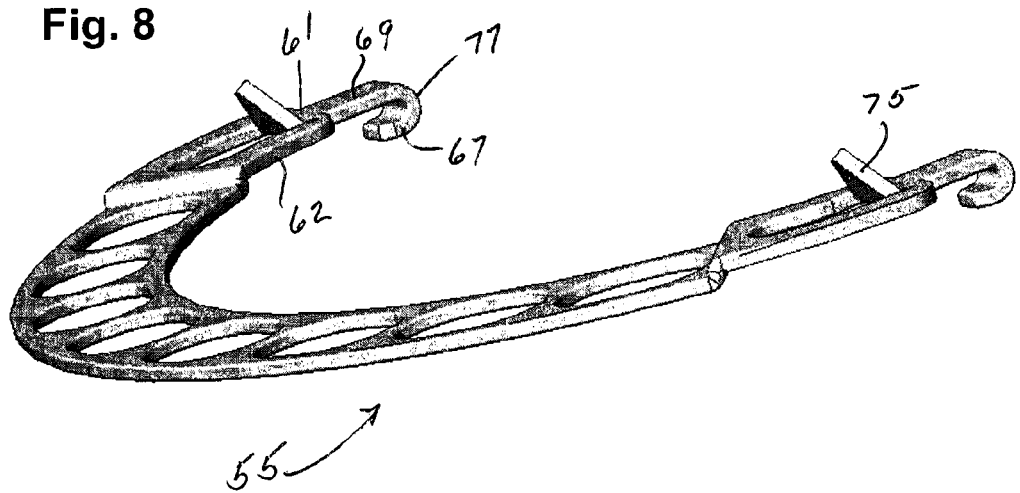
FIG. 8 is a similar perspective view of the semicircular piece of the ring of FIG. 5.
Figure 9:
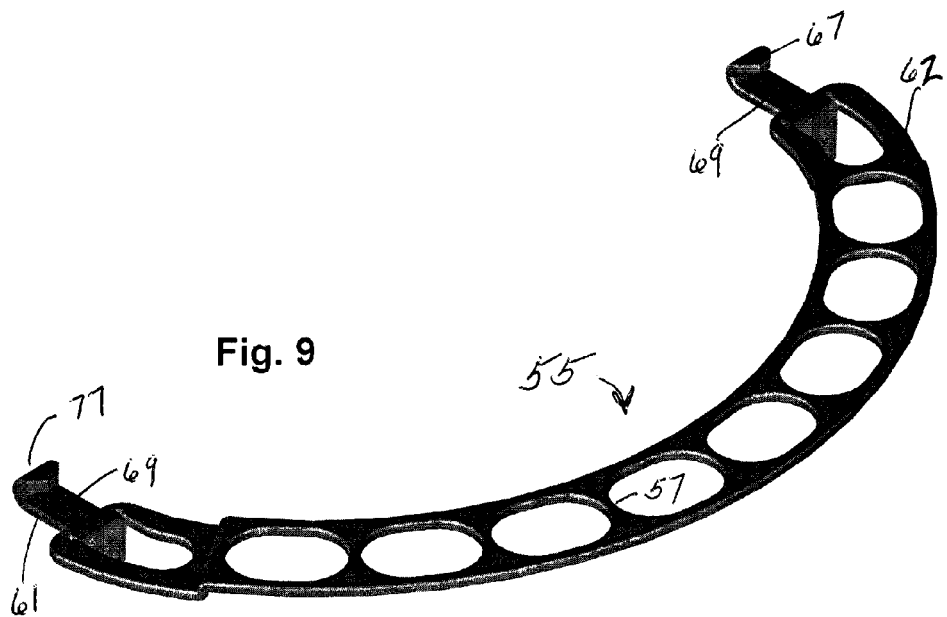
FIG. 9 is a perspective view of the semicircular piece of FIG. 8 taken from the opposite or rear side.
Figure 10:
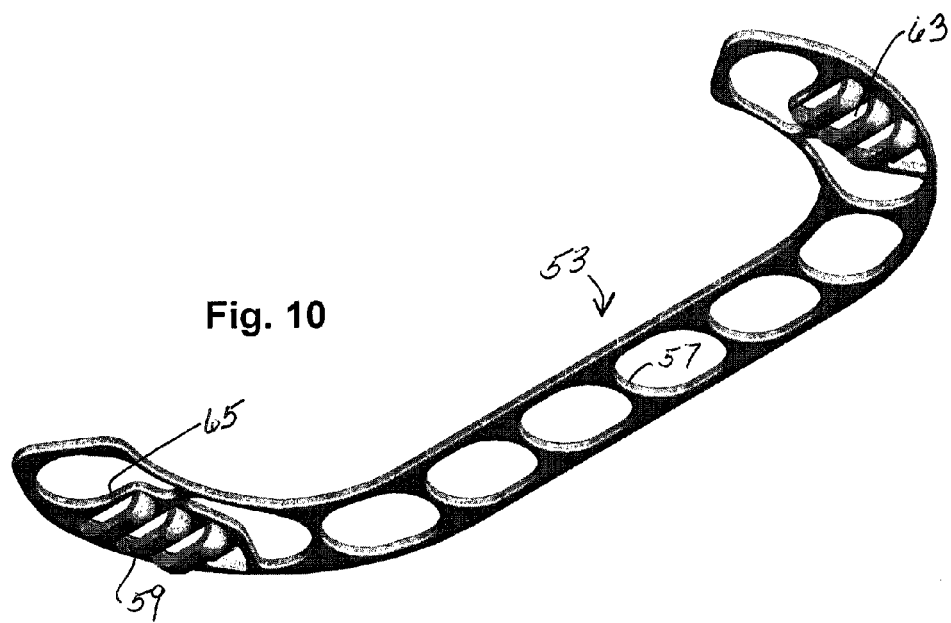
FIG. 10 is a perspective view of the straight piece of FIG. 7 taken from the opposite or rear side.

As best seen in FIG. 7, the interconnecting parts 59 in the end sections or arms of the straight piece 53 comprise a series of three pockets 63 aligned in a row. As best seen perhaps in FIG. 10, which is a view from the rear side of the piece 53, the pockets 63 are punched or pressed out of the flat stock in a manner so as to create a short bar 65 along the edge of the pocket that is nearest the end of the arm. The semicircular piece 55 is formed with an interconnecting part 61 having the general form of a hook which has a reentrant triangular tang 67 that is proportioned so as to be received in any one of the three pockets 63 formed in each arm of the straight piece 53. The reentrant shape of the hook end is such that the distance between the tang 67 and the shank 69 of the hook is about equal to the thickness of the stock from which the piece 53 is constructed. Accordingly, after the head or tang 67 of the hook has been received in the pocket 63, the slight movement of the two ends of the respective pieces 53, 55 away from each other causes the hook to fit over the bar 65 at the one edge of the pocket and clamp the bar between the shank 69 and the tang 67, thus locking the ring at this lateral location. To facilitate manipulation of the adjustable ring 51 and adjustment of the interconnections at the respective lateral locations, the arm at each end of the straight piece 53 is formed with a triangular ear 73 that extends upward from its front surface, and each end of the semicircular piece 55 is formed with a triangular ear 75 which extends upward from the stepped up section 62, as seen in FIGS. 7 and 8.

Figure 11:
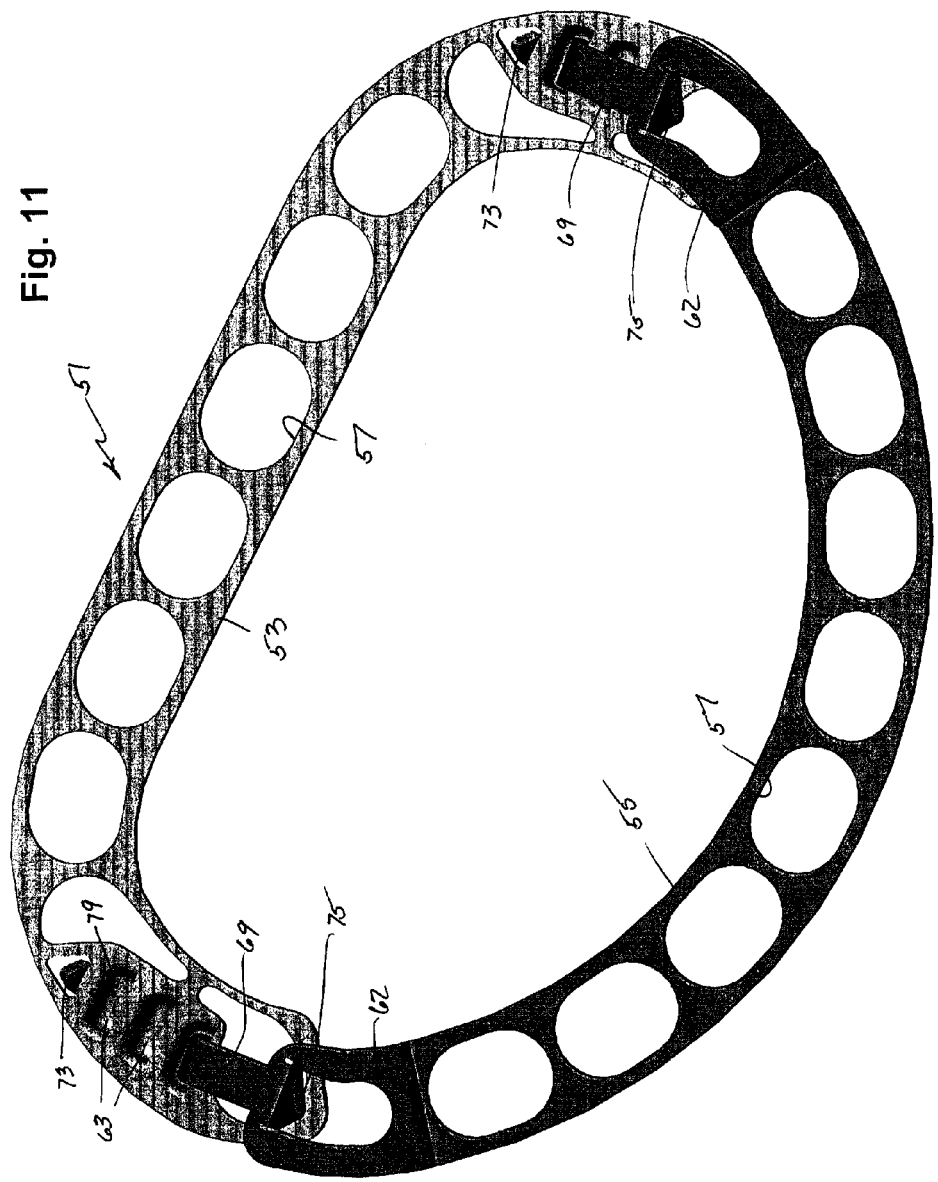
FIG. 11 is a front perspective view similar to FIG. 5 with the adjustable annuloplasty ring shown in an asymmetrical orientation.
Figure 12:
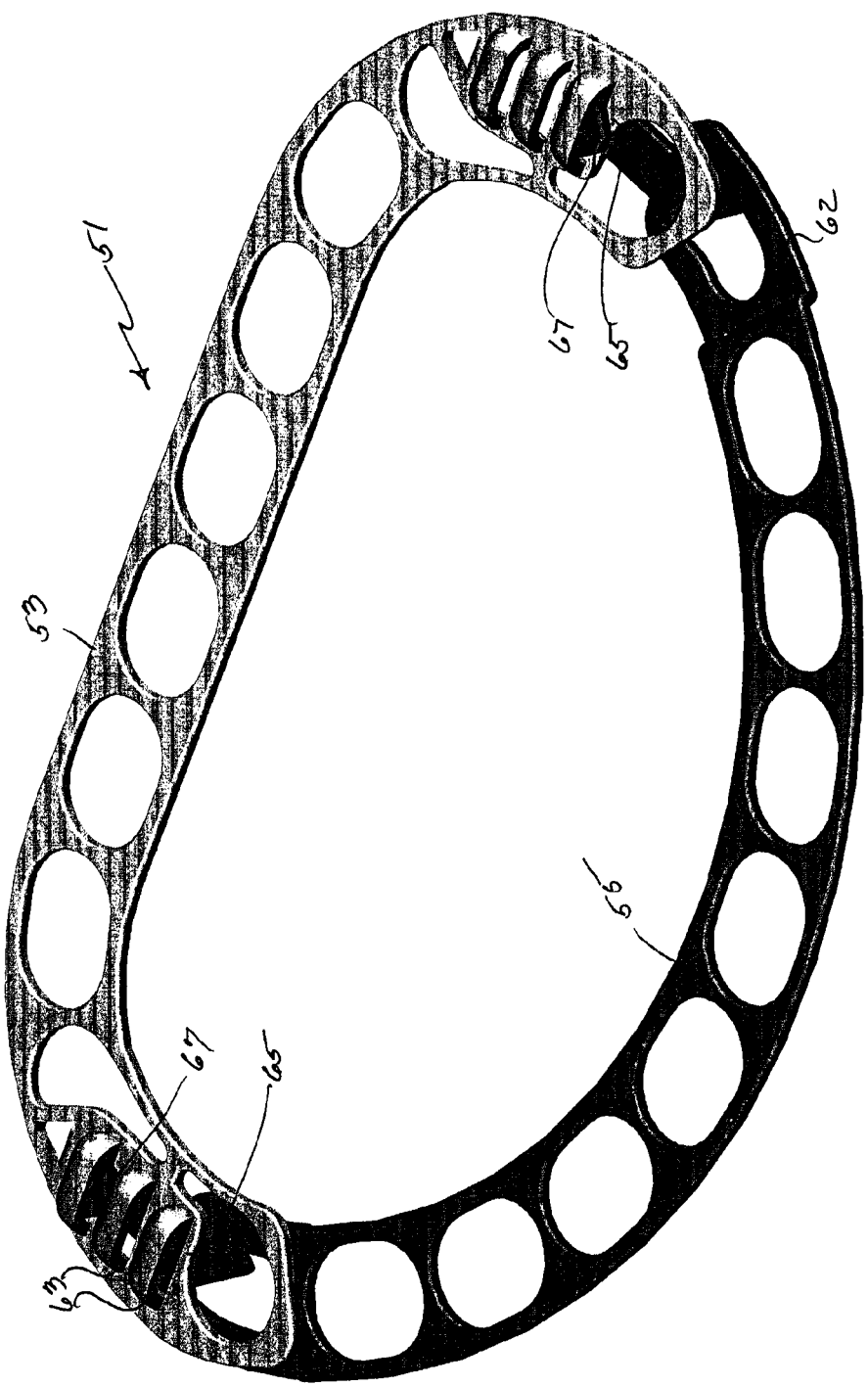
FIG. 12 is a perspective view of the ring of FIG. 11 taken from the opposite or rear side.
Figure 13:
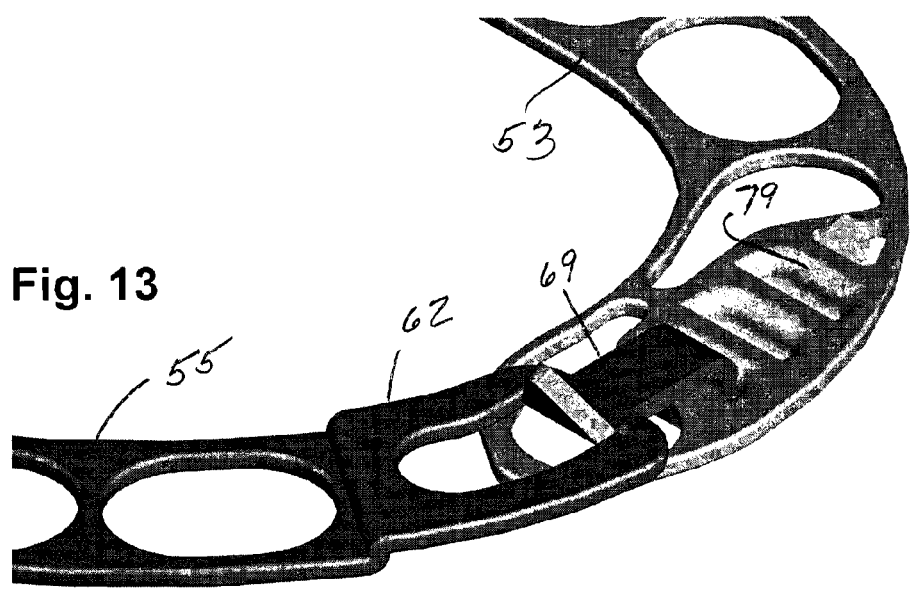
FIGS. 13, 13A, 14, and 15 are fragmentary perspective views of the ring of FIG. 5, showing the three different positions in which interconnection may be effected between the two pieces at one lateral location.
Figure 13A:
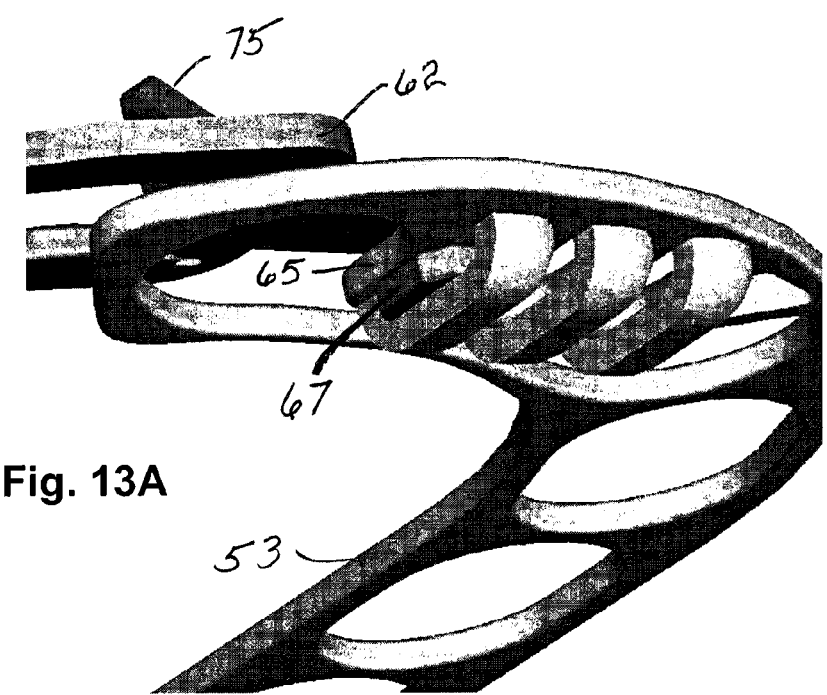
Figure 14:
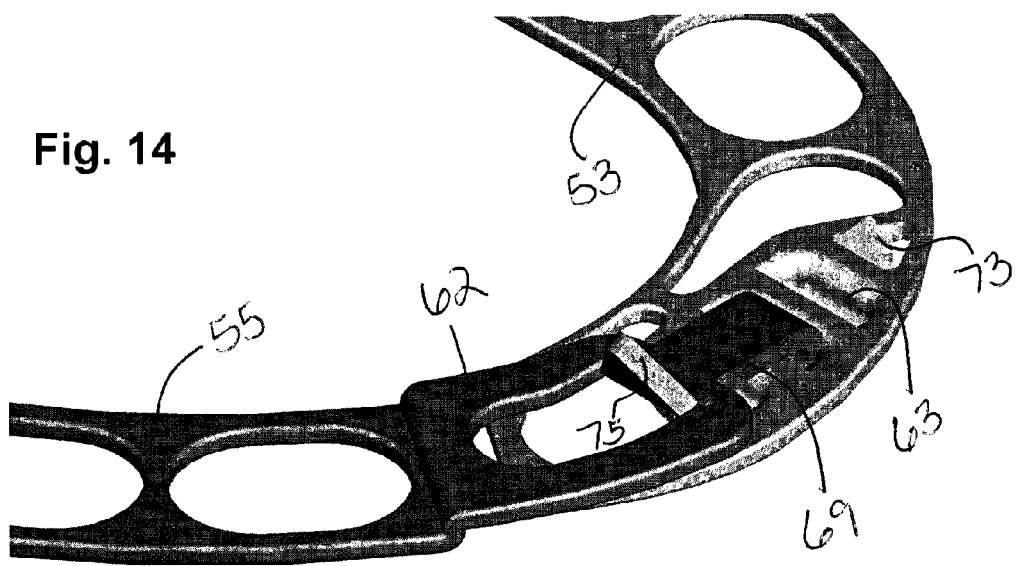
Figure 15:
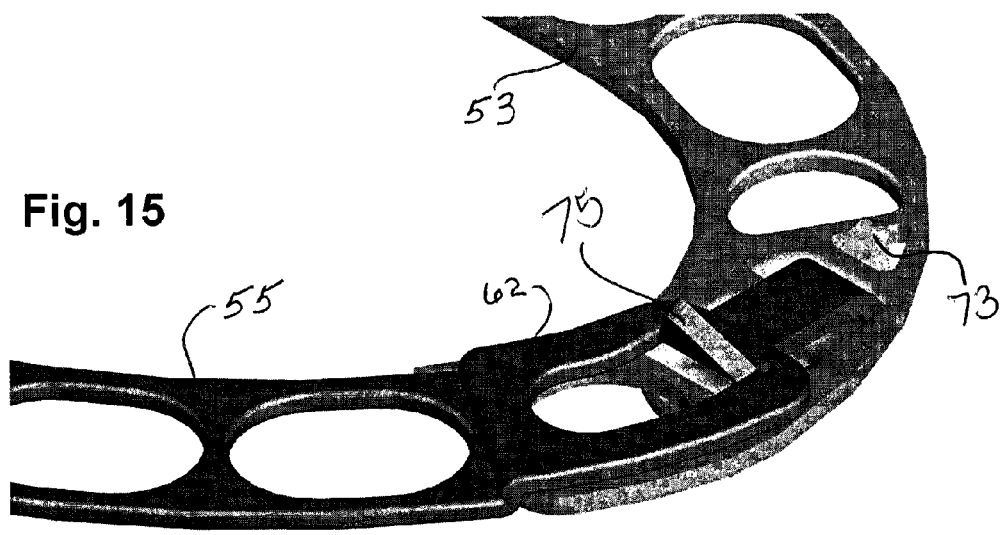

The interconnecting parts 59, 61 provide a surgeon with the ability to select one of three different incremental lengths at each lateral location of the adjustable ring 51 for the purpose of adjusting the AP diameter of the valve. The ultimate shape of the ring, when adjustment is complete and the ring 51 is secured to the heart tissue, may be one of symmetry as shown in FIGS. 5 and 6 where, for example, the hooks on both ends of the semicircular piece are received in the pocket 63 located furthest from the end of the straight piece 53, where the AP diameter will be the shortest. However, in many instances it may be desirable to adjust the ring to an asymmetrical orientation as depicted in FIGS. 11 and 12 where, for example, one of the hooks is received in a pocket 63 closest to the end of the arm of the straight piece and the other hook is received in the pocket 63 furthest from the end of the straight piece. Fragmentary views of an adjustable ring, interconnected sections are shown in FIGS. 13 and 13A with the hook section received in the pocket nearest to the end. FIGS. 14 and 15 illustrate the hook received in the center pocket and the furthest pocket.

Manipulation of the ring 51 to move the hook section of one end of the semicircular piece 55 to a different pocket 63 is easily carried out after the adjustable annuloplasty ring has been initially implanted in a mitral valve being repaired. Only a few staples or sutures are initially implanted through the windows 57 in the two pieces to orient the ring and allow the surgeon to determine the amount of coaptation of the leaflets that has been achieved; however, this initial securing of the two valve pieces to the heart valve tissue is sufficient to maintain the juxtaposed orientation of the surfaces of the respective end sections of the pieces 53 and 55. Then, for example, if the surgeon wishes to shorten the length of one or both lateral regions of the initially implanted ring, the upstanding ears 73 and 75 can be simply squeezed toward each other a sufficient distance so that the hook is displaced from the pocket 63 in which it initially resides. Such is facilitated as a result of the arcuate end surface 77 of the hook camming against the canted surface 79 of the wall of the pocket which faces the bar 65; this causes the hook to rise up and slide out of its initial pocket. Depending upon the amount of shortening desired, the hook can be aligned either with the center pocket (FIG. 14) or with the furthermost pocket (FIG. 15) in which it will be likewise received. Once the desired alignment is obtained, grasping the two ears 73, 75 and moving them slightly apart from each other will cause the hook to grasp the bar 65 of that particular pocket between the tang 67 and the shank 69 and lock this lateral location of the adjustable ring, as best seen in FIG. 13A. As mentioned with regard to the embodiment of FIGS. 1-4, the initial securing of the ring 51 to the heart valve tissue through the combination of the elongated windows 57 and staples or suturing permits such adjustment or fine-tuning of the length of either or both lateral regions of the ring to take place after the ring has been initially implanted. Once the optimal coaptation of the leaflets has been achieved, additional staples and/or sutures are installed, and insertion of such through aligned openings in the juxtaposed end sections will lock the final adjustment, if desired.

Illustrated in FIGS. 16-23 is another alternative embodiment of an adjustable annuloplasty ring 81 embodying various features of the invention designed for the repair of a mitral valve. The construction embodies two interlocking pieces or parts that can be adjusted with respect to each other at two lateral locations similar to the annuloplasty rings 11 and 51, to effect a change in the length of the circumference of the ring; however, the construction is such as to provide a hinged connection at both lateral locations so that one piece can pivot with respect to the other so that they can lie in slightly varying planes.

Figure 20:
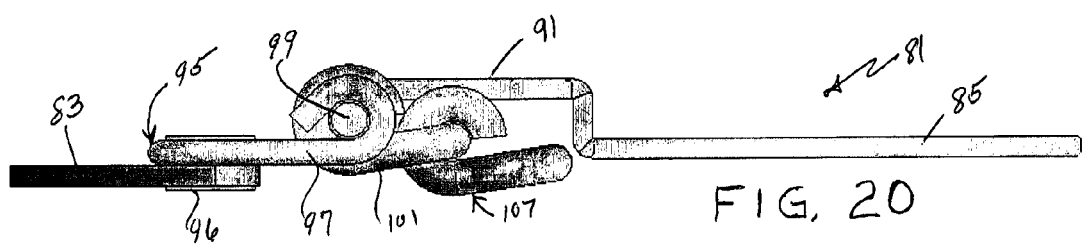
FIG. 20 is a left side view of the ring of FIG. 18.

The ring 81 is formed from two pieces or parts: a substantially straight piece 83 and a semicircular piece 85, both of which are of substantially linear form and have a plurality of elongated windows 87 regularly spaced along their lengths. End portions 89 of the semicircular piece 85 are again stepped upward toward the front surface a distance equal to the thickness of the bar stock material from which the straight piece 83 is formed. The end portion is fashioned to form a hook 91 having a tang 92 at its end which is bent over at 180 degree U-shaped bend from the shank 93 of the hook, generally similar to the interconnector at the end of the semicircular part 55. Instead of forming an interconnector integrally as a part of the straight piece 83, a short base interconnector 95 is pivotally attached to each end of the piece to provide a pair of short parallel end portions having the ability to pivot laterally or centrally in the general plane of the ring allowing fine angle adjustments between the two pieces. Affixation can be made in any suitable manner, as by using a hollow rivet 96 as illustrated or some other suitable pivot. The base interconnectors 95 are formed with a pair of parallel arms 97 which are curled upward about the respective end of a short cylindrical rod 99 so that the rod is rotatably journaled in the bight of the curled ends, as best seen in FIG. 20; the rod 99 serves as a first crossbar which can rotate freely. A first extension unit 101 is connected to the rod 99 so as to extend the interconnector 95 further from the straight piece 83 and provide a second hinge axis. The first extension unit 101 can be formed of cylindrical rod that is bent to provide a second transverse crossbar 103 at its end and to attach to the cylindrical first crossbar 99 of the base interconnector 95 by similarly curling the ends of its two arms 105 around the crossbar. It can frictionally grip the crossbar rod 99, thus securing its pivotal attachment in the curled ends of the base interconnector 95. A second extension unit 107 of similar construction is attached to the second cylindrical crossbar 103 of the first extension unit 101 and provides a third transverse cylindrical crossbar 109 at the end thereof and thus a third hinge axis. Its arms 111 are similarly curled around the second crossbar 103 to provide a pivotal connection therewith at the second hinge axis.

As can be seen from the drawings, interconnection of the two pieces 83,85 is effected by interengaging the hooks 91 at the ends of the semicircular piece 85 with one of the transverse cylindrical crossbars 99, 103, 109 that is a part of each interconnector assembly at each end of the straight piece 83. The distance between the tang 92 and the shank 93 of the hook is optionally set so that it will either tightly frictionally engage any one of the three cylindrical crossbars of the interconnector assembly or will snap onto the crossbar and be pivotally received thereon. In the latter instance, the connection permits the hook 91 to rotate about the cylindrical crossbar so as to effect relative pivoting and thus hinged movement of one piece relative to the other; however, minor hinging may also occur at the other hinge axes. The ability of the base interconnectors 95 to pivot allows maximal surface contact to be achieved between the inner surface of the hook and a respective crossbar 99, 103, 109.

Figure 16:
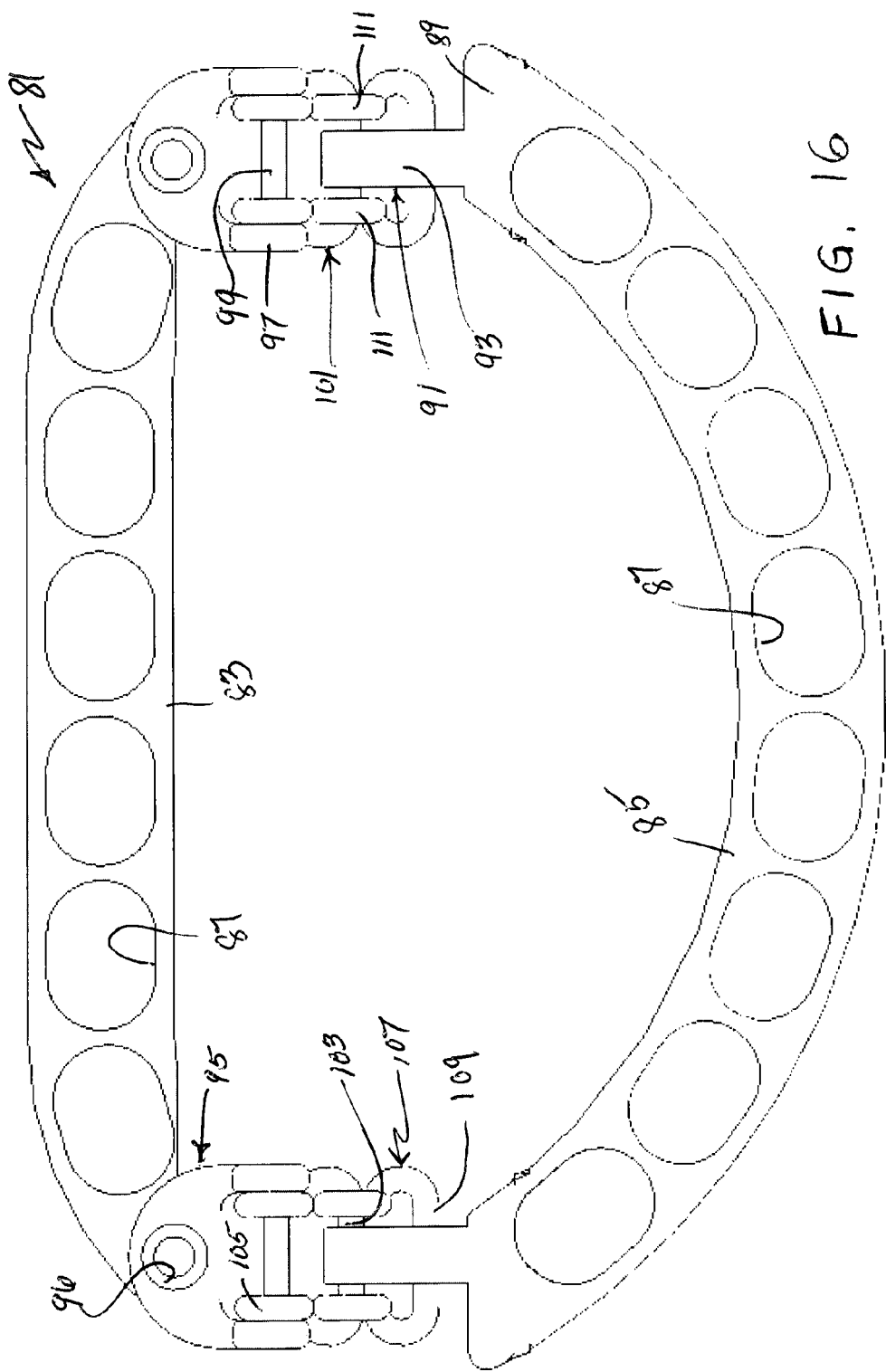
FIG. 16 is a plan view of an alternative adjustable two-piece annuloplasty ring embodying various features of the present invention which adds a hinge feature, with the two pieces shown interconnected in symmetrical orientation with an intermediate AP diameter adjustment.
Figure 17:
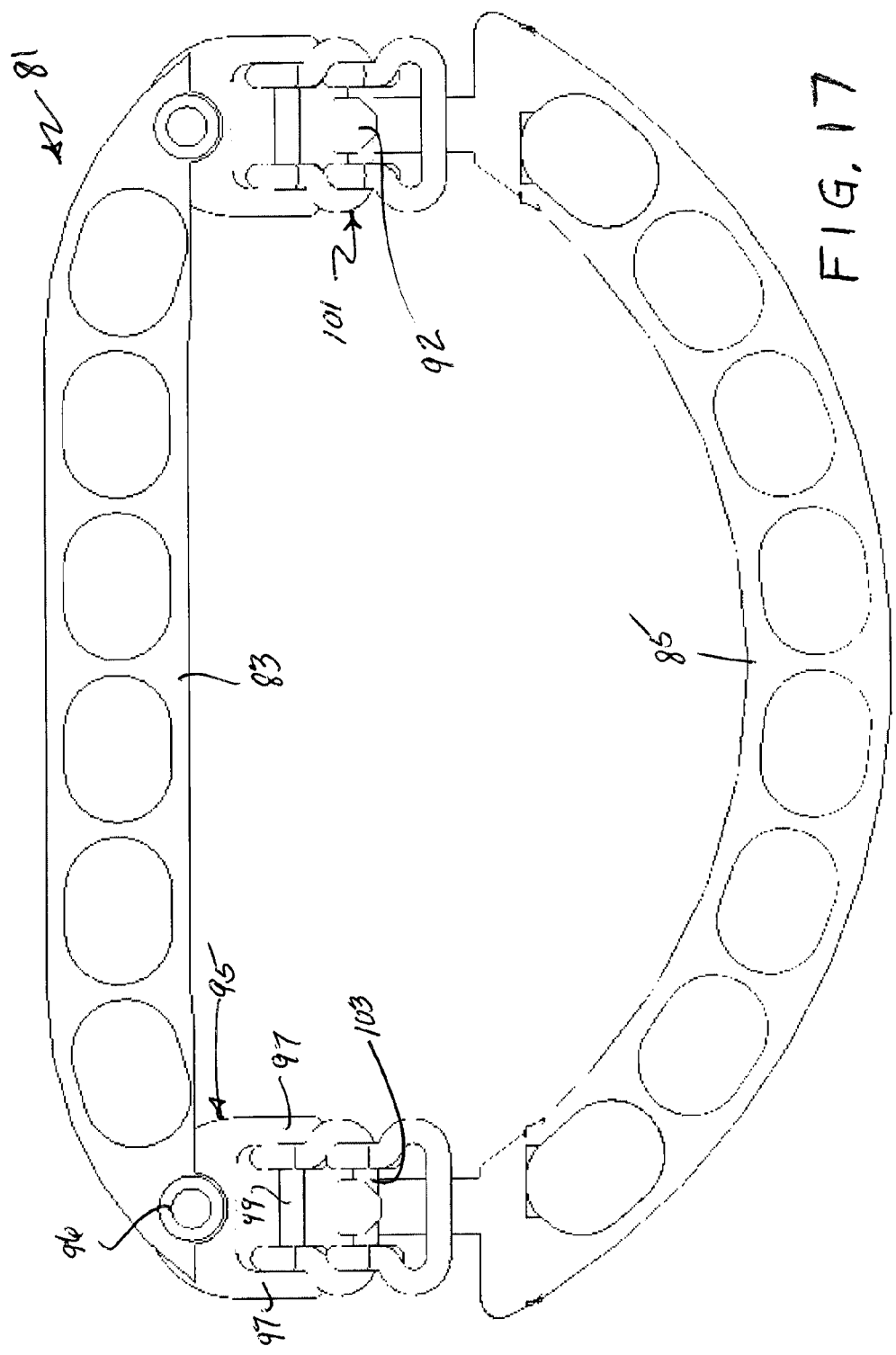
FIG. 17 is a bottom view of the ring of FIG. 16 taken from the opposite or rear side.
Figure 18:
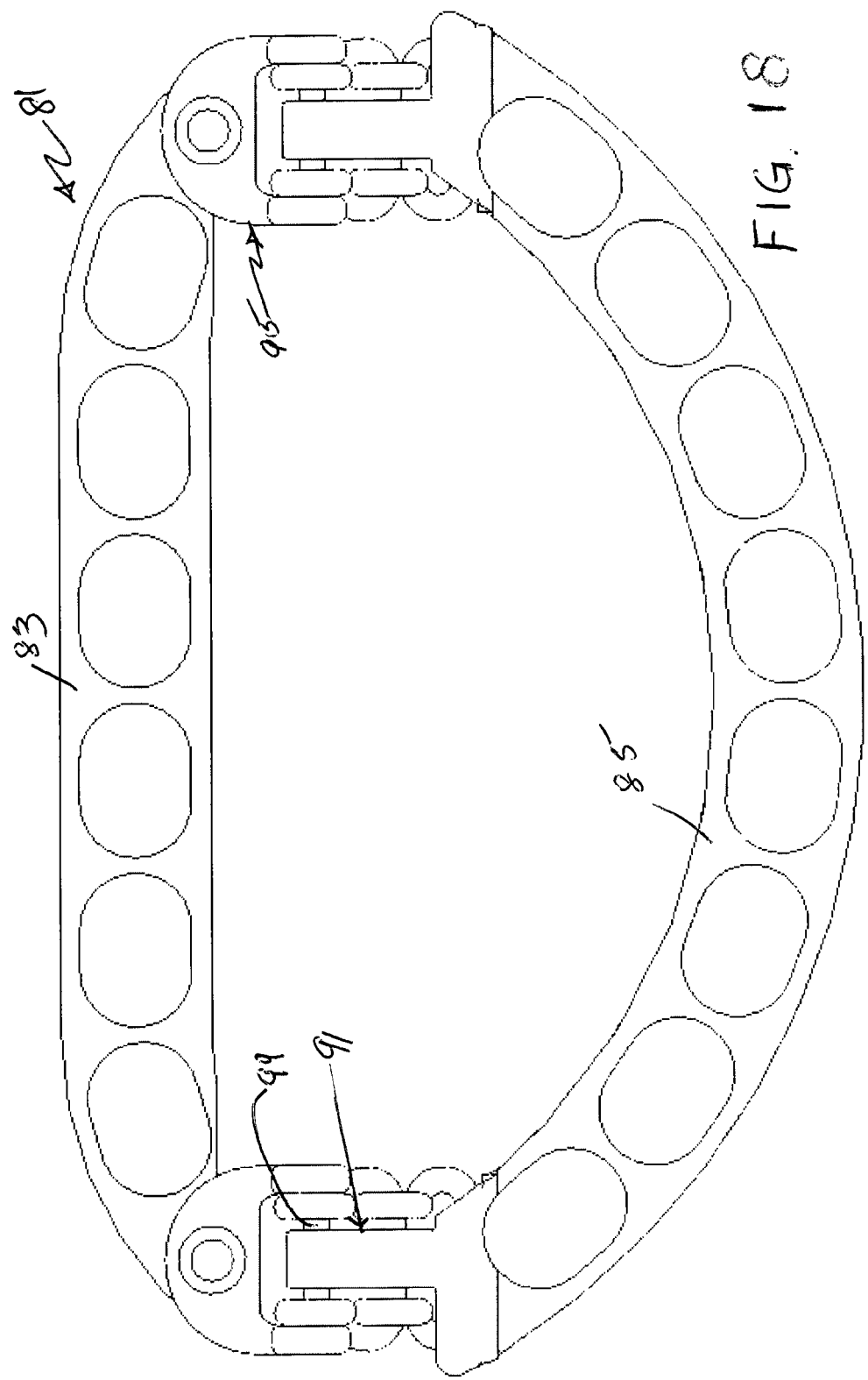
FIG. 18 is a plan view similar to FIG. 16 with the two pieces interconnected with a shorter AP diameter adjustment.
Figure 19:
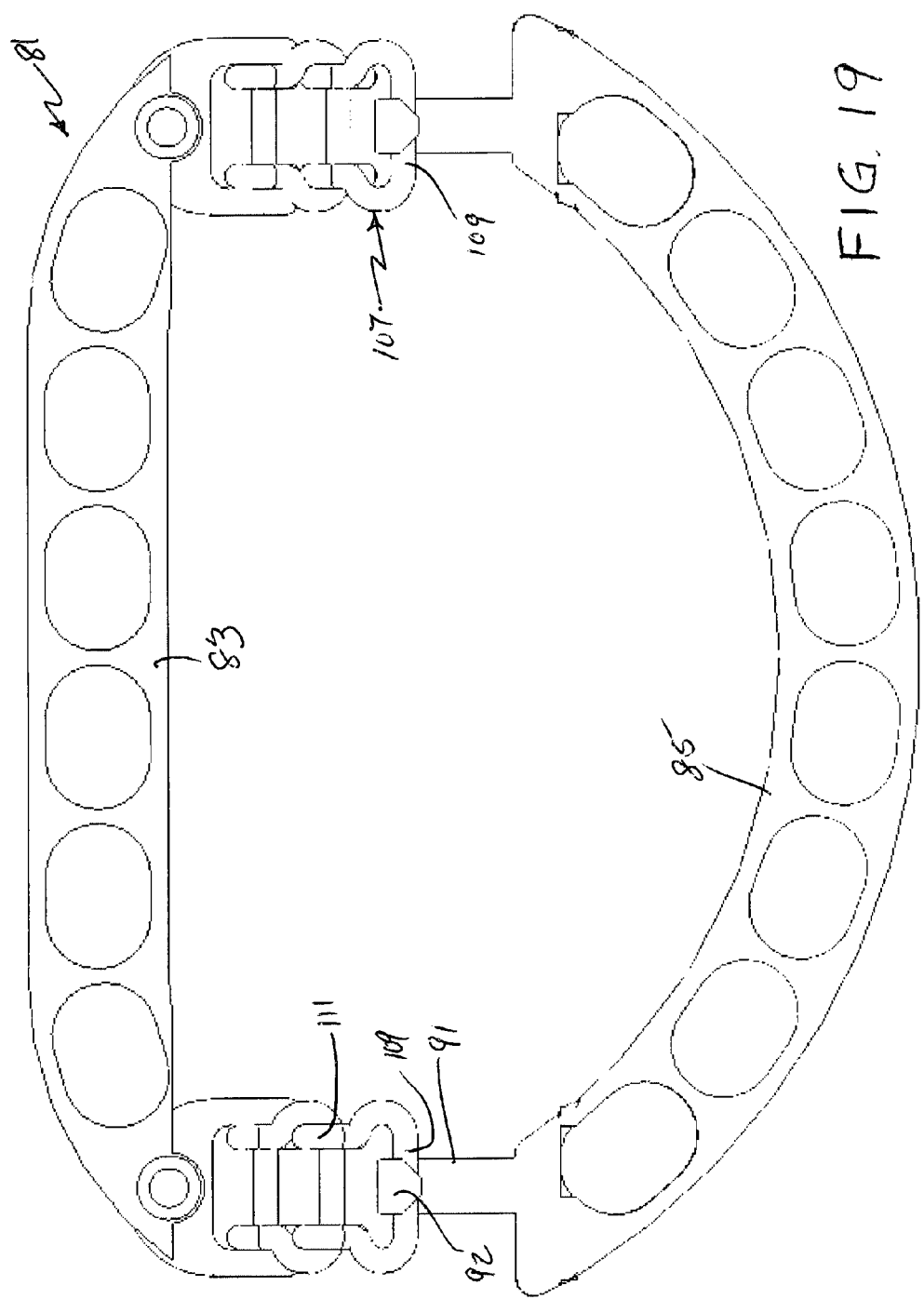
FIG. 19 is a bottom view similar to FIG. 17 with the two pieces interconnected with a longer AP diameter adjustment.

FIG. 16 shows symmetrical interengagement of the two hooks 91 with the central or second crossbar 103 which is a part of the first extension unit 101. FIG. 17, which is taken looking at the opposite or bottom surface of the ring, better shows the central crossbar 103 seated in the head of the hook 91. FIG. 18 shows symmetrical engagement of the two hooks 91 with the crossbar 99 of the interconnector 95, i.e. the crossbar nearest the straight piece, so that engagement therewith would effect the shortest AP diameter. FIG. 19 shows the ring viewed from the bottom side with the two hooks 91 symmetrically engaged with the cylindrical crossbars 109 of the second extension unit 107, thus providing the greatest AP diameter. All three of the orientations illustrated are symmetrical; however, asymmetrical adjustment of the interconnection means at the two lateral locations is possible due to the base connectors 95 being pivotally attached to the straight piece 83 so they can swing in either direction. This mechanism allows fine bilateral angle correction/adaptation/adjustment/movement where there is asymmetry in the hook positions on crossbars 99, 103 and 109 and assures free hinged movement between the two pieces 83,85 in such an asymmetric arrangement.

Figure 21:
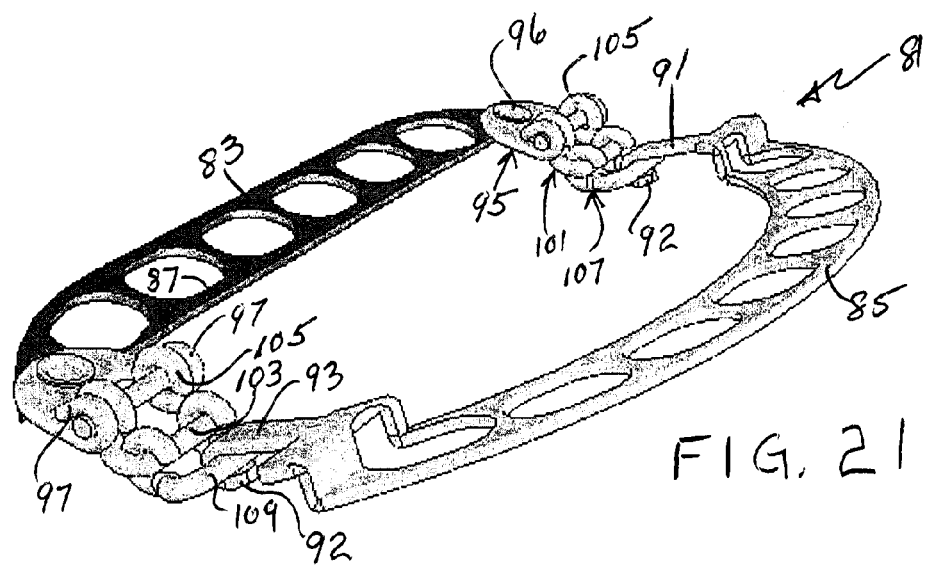
FIG. 21 is a perspective view of the ring of FIG. 19 showing the semicircular piece pivoted upward from the plane of the straight piece.
Figure 22:
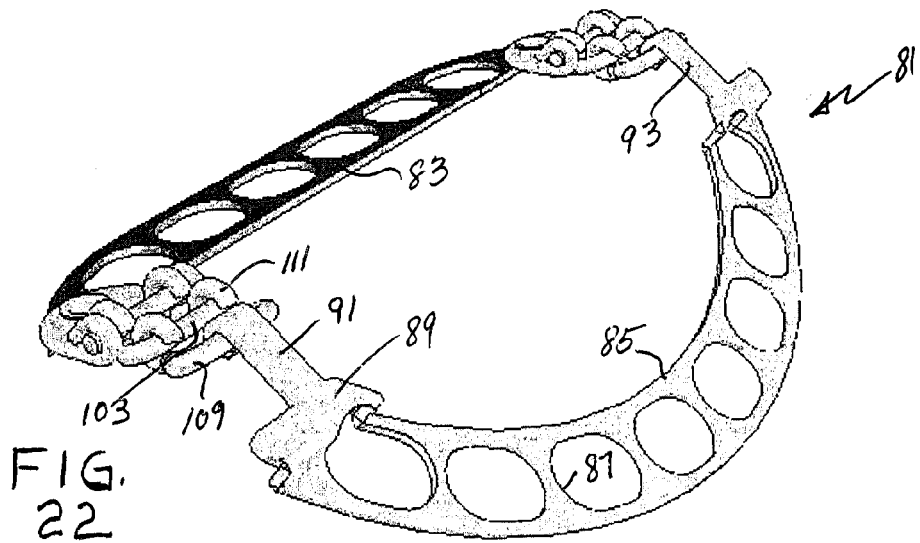
FIG. 22 is a perspective view similar to FIG. 21 with the semicircular piece of the ring pivoted downward from the plane of the straight piece.

FIG. 20 is a left side view of the ring shown in FIG. 18 where the adjustment is such as to create the shortest AP diameter. The two substantially planar pieces 83,85 are shown in substantial alignment with each other. FIG. 21 shows the ring adjusted to provide the largest AP diameter, as illustrated in FIG. 19, with the orientation of the two pieces 83,85 showing hinged movement of one piece relative to the other so that the semicircular piece is disposed above the upper surface of the straight piece. Hinge movement occurs mainly with the hook pivoting on the crossbar 109, but there may be some at the other two hinge axes. FIG. 22 illustrates the same ring with the hinged movement in the opposite direction so that the semicircular piece 85 lies substantially at a level below that of the upper surface of the straight piece 83, with the primary but not necessarily the only pivotal movement occurring about the crossbar 109.

This ability of the two parts, after final adjustment has been made by the surgeon to establish the appropriate AP diameter that accomplishes the best coaption of the leaflets, to hinge slightly in either direction, as the natural valve does to some degree, adds a further feature/dimension/quality to the annuloplasty repair ring. This added feature allows the ring to constantly follow the relative cyclic movements of the natural valve without restricting its movement nor that of the anterior and the posterior leaflets of the native valve. Moreover, the establishment of multiple hinge axes at each lateral location further facilitates the hinge movement accommodating valves of slightly different sizes and shapes.

Figure 23:
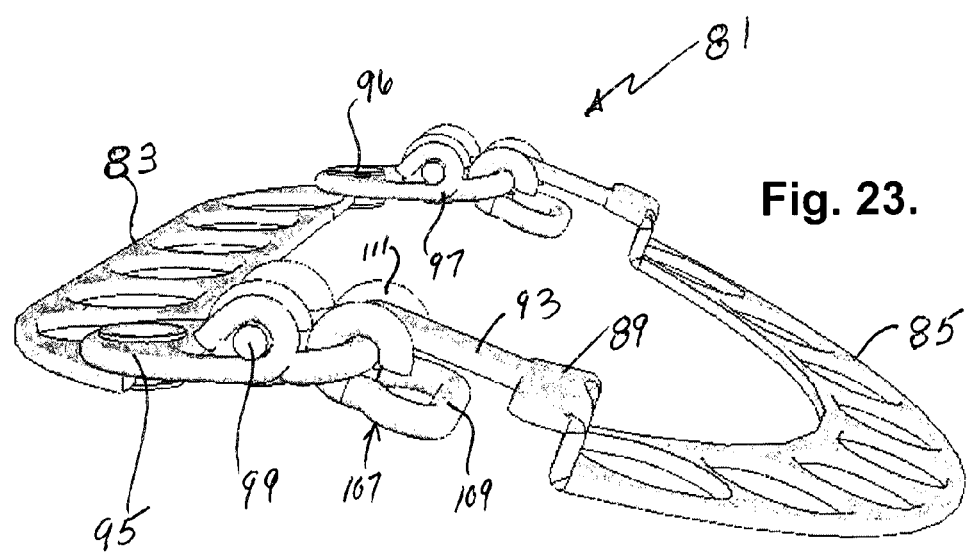
FIG. 23 is a perspective view similar to FIG. 22 with the two pieces shown in the intermediate adjustment position of FIG. 16.

When the hook 91 is engaged with the cylindrical crossbar 109 at the very end of the interconnector assembly, as seen in FIGS. 21 and 22, hinged movement in either direction is likely primarily by pivotal movement of the hook but there may be lesser movement at the other axes. Such hinged movement is depicted in FIG. 21 where the semicircular piece 85 moves to an orientation above the surface of the straight piece 83 and in FIG. 22 where it moves hingedly therebelow. However, when the interconnection is adjusted to connect the hooks 91 with the cylindrical crossbar 103 so as to effect a shorter AP diameter, pivoting about multiple axes at one or both lateral locations may more likely occur. FIG. 23 shows the ring where the adjustment is to the intermediate location with the hook 91 engaging the cylindrical crossbar 103 of the first extension unit 101. Because the extension units 101, 107 respectively have the pivotal axes at the cylindrical crossbars 99, 103, they can freely pivot. The construction is preferably such as to also permit free pivoting of the hook 91 about the crossbar 103; thus, downward hinged movement as shown in FIG. 23 can result in pivoting of the first extension unit 101 at the hinge axis 99 and of the hook 91 and second extension unit at the crossbar 103. As mentioned above, the pivotal connection of the base interconnectors 95 allows swinging in a plane parallel to the plane of the linear straight piece 83 and facilitates asymmetric interconnection at the two lateral locations.

Although the invention has been illustrated and described with respect to certain preferred embodiments, which constitute the best modes known to the inventor at this time, it should be understood that various changes and modifications that would be obvious to one of ordinary skill in this art may be made without departing from the scope of the invention which is defined by the claims appended hereto. For example, although rings are illustrated for repair of a mitral valve, rings of an appropriate shape are likewise contemplated for similar repair of a leaking tricuspid valve. Although the three illustrated embodiments both employ two interconnections at lateral spaced apart locations, three or more such interconnections can be incorporated, if desired. For example, as mentioned with respect to the FIG. 1-4 embodiment, one or more additional interconnections could be provided in an adjustable ring 51 such as that illustrated in FIGS. 5 and 6, if for example it were desired to incorporate an ability to also change the long axis of the ring.

Changes may also be made to the attachment interconnections for the hinged rings shown in FIGS. 16-23. For example, the hooks and crossbars might be reversed, with the hooks formed at the ends of the straight piece. Moreover, shown in FIG. 24 is an alternative embodiment of such a hinged annuloplasty ring 81a wherein the straight piece 83a is formed with curved ends so as to closely resemble the straight parts 13 and 53 of the earlier described rings. The interconnectors are similarly pivotally connected to the ends of the straight piece 83a by hollow rivets 96 or the like. This construction offsets the longitudinal axis about which the two-piece construction will be hinged slightly further from the centerline of the straight piece. In addition, a hook 91a is formed with a shortened shank, and end sections 89a of the semicircular piece 85a are approximately proportionally lengthened. If desired to attach the interconnectors 95 rigidly to the ends of the straight piece so that they are parallel to each other and perpendicular to the center line of the straight piece, they could be so attached by rivets or other connectors or simply by welding; however, they are preferably allowed to pivot about the hollow rivets, because such an arrangement renders the hinged ring self-adaptable to an asymmetric adjustment at the two lateral interconnections and better able to tolerate a hinge axis that is not parallel to the centerline of the straight piece.

Particular features of the invention are emphasized in the claims that follow.

The invention claimed is:

1. An annuloplasty ring comprising two separate rigid parts, the ends of each of which have mechanisms which are interconnectable to form a complete ring that will encircle a valve to be repaired, said mechanisms being located at two spaced apart lateral locations for positioning adjacent commissures of the valve and being hinged to permit movement of said rigid parts about an axis defined by the mechanisms at said spaced apart lateral locations, said mechanisms being adjustable to change the circumference of the ring and thus its diameter while the ring is at least partially secured to heart valve tissue in order to effect better coaption of valve leaflets.

2. The annuloplasty ring of claim 1 wherein said mechanisms permit hinged movement about multiple pivot axes.

3. An adjustable annuloplasty ring which comprises:
two separate anterior and posterior generally linear interconnectable parts made of generally flat, biocompatible, rigid bar stock material,
both said separate anterior and posterior rigid parts having a series of apertures spaced along the length thereof, and
a pair of said interconnection mechanisms formed at end portions of each of said anterior and posterior rigid parts, the pairs of interconnection mechanisms are designed to slidably engage each other to adjustably connect said separate anterior and posterior parts to form a complete ring, with one said pair of said interconnection mechanisms each including a toothed bar that is oriented perpendicular to the plane of the flat rigid material and with the other pair of said interconnection mechanisms including structure for adjustably engaging said toothed bar during slidable engagement between said interconnection mechanisms, the ring is shaped and proportioned to surround a human mitral valve, with said interconnection mechanisms located at lateral locations for positioning adjacent the commissures of the valve, so that adjustment at said interconnection mechanisms will effect an increase or a decrease in the AP diameter of the valve while said parts are secured to mitral valve tissue.

4. The adjustable annuloplasty ring of claim 3 wherein said structure in said other pair of interconnection mechanisms includes a plurality of parallel rods that are spaced-apart distances similar to the spacing of teeth on said toothed bars and said other pair of interconnection mechanisms each also includes an elongated channel adjacent to said parallel rods, and wherein each said toothed bar is elongated and is slidably receivable in said channel in one of the other pair of interconnection mechanisms to allow adjustment of the AP diameter of the valve while both said anterior and posterior rigid parts are attached to the heart tissue.

5. The adjustable annuloplasty ring of claim 4 wherein said interconnection mechanisms are formed with engageable structure which allows squeezing to move said end portions toward each other to reduce the AP diameter of the valve.

6. The adjustable annuloplasty ring of claim 5 wherein said engageable structure comprises ears extending upward from the surface of said rigid parts.

7. An adjustable annuloplasty ring which comprises:
first and second generally linear interconnectable parts made of generally flat, biocompatible bar stock material,
each said part having a series of apertures spaced along the length thereof and having end portions comprising pairs of interconnection mechanisms,
said pairs of interconnection mechanisms at the end portions of said first and second interconnectable parts being designed to adjustably connect said respective end portions at lateral locations to form a complete ring which is shaped and proportioned to surround a human mitral or tricuspid valve,
said pairs of interconnection mechanisms respectively comprising hooks having re-entrant heads and connectors including a series of crossbars of cylindrical shape,
wherein an axis of hinged connection is defined by each of said crossbars, which axes are each generally parallel to the long axis of the valve being repaired, so that hinged movement is permitted about multiple axes at each lateral location, and wherein adjustment of the annuloplasty ring at said pairs of interconnection mechanisms changes the AP diameter of the valve which the annuloplasty ring surrounds.

8. An adjustable annuloplasty ring which comprises:
anterior and posterior generally linear interconnectable parts made of generally flat, biocompatible, rigid bar stock material, both said anterior and posterior rigid parts having a series of apertures spaced along the length thereof, and
a pair of said interconnection mechanisms formed at end portions of each of said anterior and posterior rigid parts, one said pair of interconnection mechanisms each comprising a hook which has a re-entrant head and the other said pair of interconnection mechanisms each being formed with a series of crossbars that can be selectively engaged by said hook, the pairs of interconnection mechanisms are designed to slidably engage each other to adjustably connect said separate anterior and posterior parts to form a complete ring which is shaped and proportioned to surround a human mitral valve, with said interconnection mechanisms located at lateral locations for positioning adjacent the commissures of the valve, so that adjustment at said interconnection mechanisms will effect an increase or a decrease in the AP diameter of the valve while said parts are secured to mitral valve tissue.

9. The adjustable annuloplasty ring of claim 8 wherein said series of crossbars are provided by edges of a series of pockets in the respective end portions, and wherein said hooks are proportioned to be received in said pockets and to clampingly engage said crossbars upon relative movement of said end portions of said interconnectable parts away from each other so as to lock together the respective end portions.

10. The adjustable annuloplasty ring of claim 8 wherein said interconnection mechanisms are formed with upstanding ears which allows said ears to be squeezed toward each other to move said end portions toward each other to reduce the AP diameter of the valve.

* * * * *